United States Patent
Delaune et al.

(10) Patent No.: US 11,534,374 B2
(45) Date of Patent: Dec. 27, 2022

(54) TOPICAL COMPOSITION

(71) Applicant: DSM IP ASSETS B.V., Heerlen (NL)

(72) Inventors: Mathilde Delaune, Kaiseraugst (CH); Christine Mendrok-Edinger, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 143 days.

(21) Appl. No.: 16/954,687

(22) PCT Filed: Dec. 17, 2018

(86) PCT No.: PCT/EP2018/085106
§ 371 (c)(1),
(2) Date: Jun. 17, 2020

(87) PCT Pub. No.: WO2019/121442
PCT Pub. Date: Jun. 27, 2019

(65) Prior Publication Data
US 2020/0383884 A1    Dec. 10, 2020

(30) Foreign Application Priority Data
Dec. 19, 2017  (EP) .................................... 17208374

(51) Int. Cl.
| | |
|---|---|
| *A61K 8/06* | (2006.01) |
| *A61K 8/35* | (2006.01) |
| *A61K 8/37* | (2006.01) |
| *A61K 8/42* | (2006.01) |
| *A61K 8/49* | (2006.01) |
| *A61K 8/73* | (2006.01) |
| *A61K 8/67* | (2006.01) |
| *A61K 8/55* | (2006.01) |
| *A61Q 17/04* | (2006.01) |

(52) U.S. Cl.
CPC ................ *A61K 8/062* (2013.01); *A61K 8/35* (2013.01); *A61K 8/37* (2013.01); *A61K 8/42* (2013.01); *A61K 8/4966* (2013.01); *A61K 8/55* (2013.01); *A61K 8/673* (2013.01); *A61K 8/73* (2013.01); *A61Q 17/04* (2013.01); *A61K 2800/412* (2013.01); *A61K 2800/59* (2013.01)

(58) Field of Classification Search
None
See application file for complete search history.

(56) References Cited

U.S. PATENT DOCUMENTS

| | | | |
|---|---|---|---|
| 2015/0265510 A1* | 9/2015 | Johncock | A61K 8/26 424/59 |
| 2017/0360666 A1* | 12/2017 | Pottie | A61K 8/37 |

FOREIGN PATENT DOCUMENTS

| | | |
|---|---|---|
| EP | 2 921 157 | 9/2015 |
| EP | 3 093 007 | 11/2016 |
| WO | 2016/134846 | 9/2016 |

OTHER PUBLICATIONS

International Search Report for PCT/EP2018/085106 dated Feb. 11, 2019, 3 pages.
Written Opinion of the ISA for PCT/EP2018/085106 dated Feb. 11, 2019, 6 pages.

\* cited by examiner

*Primary Examiner* — Dominic Lazaro
(74) *Attorney, Agent, or Firm* — Nixon & Vanderhye P.C.

(57) ABSTRACT

The present invention relates to topical compositions comprising panthenol, hydroxyacetophenone and a micronized UV filter.

6 Claims, No Drawings

TOPICAL COMPOSITION

This application is the U.S. national phase of International Application No. PCT/EP2018/085106 filed Dec. 17, 2018 which designated the U.S. and claims priority to EP Patent Application No. 17208374.3 filed Dec. 19, 2017, the entire contents of each of which are hereby incorporated by reference.

The present invention relates to topical compositions comprising panthenol, a hydroxyacetophenone and a micronized UV filter.

Sun care products have evolved considerably over the years. Earlier formulations were intended to protect the user from UV-B radiation as was once thought that UV-B rays were the most important contributors to wrinkling, skin disease, and skin cancer. However, more recent studies have shown that UV-A radiation is equally or even more important in the development of solar damage and skin diseases, such as lupus erythematosus and melanoma and non-melanoma skin cancer. Thus, today's focus is towards eliminating as much of UVA (320-400 nm) and/or UVB (280-320 nm) light as possible. Consequently, there's a constantly increasing need for sun care products exhibiting high SPF's (Sun Protection Factor) and high UVA protection while being photostable.

Moreover, today's sun care products need skin-friendly preservatives or preservative boosters, which can be an alternative to conventional preservatives. Another need of sun care products is to improve moisturization and prevent or reduce irritations on the skin.

However, sun care products often contain significant amounts of fats and oils which after application on the skin, in particular on the fingers, often leads to an unwanted transfer of such fats and oils to surfaces such as touch screens which makes the surface smeary which is highly unwanted by the end consumer.

It was therefore the object of the present invention to remedy the disadvantages of the prior art and to develop sun care products comprising one or more UV filters, a mild preservative and a soothing agent which overcome the above outlined drawbacks.

Surprisingly, it has been found that compositions comprising a specific soothing agent and a specific preservative in combination with a micronized UV filter exhibit a significantly reduced transfer of the composition onto glass surfaces such as touch screens.

Thus, the invention relates in one aspect to topical compositions comprising panthenol, a hydroxyacetophenone and a micronized UV filter.

The term "topical" is understood here to mean external application to keratinous substances, which are in particular the skin, scalp, eyelashes, eyebrows, nails, mucous membranes and hair, preferably the skin.

Panthenol (INCI) is also referred to as D-panthenol, dexpanthenol, provitamin B5, or (+)-(R)-2,4-dihydroxy-N-(3-hydroxypropyl)-3,3-dimethylbutyramid. Panthenol improves hydration, reduces itching and inflammation of the skin, improves skin elasticity, and accelerates epidermal wound healing. Panthenol is e.g. commercially available as D-panthenol at DSM Nutritional Products Europe Ltd.

The term hydroxyacetophenone refers to o-, m- or p-hydroxyacetophenone. Particularly preferred in all embodiments of the present invention is p-hydroxyacetophenone [CAS 99-93-4] which is also called 1-(4-hydroxyphenyl)-ethanone and which is e.g. commercially available at Symrise as SymSave® H and which is a multifunctional cosmetic ingredient with anti-oxidant and soothing characteristics. It can be used as a preservation booster which is mild and safe.

The term "micronized" as used herein generally refers to a particle size $D_v50$ of less than 200 nm, preferably from about 5 nm to about 200 nm, more preferably from about 15 nm to about 100 nm (Beckmann Coulter).

Examples for micronized UV filters are micronized insoluble, organic UV filters or micronized inorganic UV filters. Examples for micronized insoluble, organic UV filters are methylene bis-benzotriazolyl tetramethylbutylphenol or tris-biphenyl triazine. Examples for micronized inorganic UV filters are micronized titanium dioxide, micronized zinc oxide, micronized cerium oxide or micronized iron oxide.

The term 'insoluble' as used herein refers to an UV absorber which exhibits a solubility at RT (i.e. ~22° C.) in common cosmetic oils such as e.g. $C_{12-15}$ alkyl benzoate, propyleneglycol, mineral oil but also in water of less than 0.05 wt.-%, preferably of less than 0.3 wt.-%, most preferably of less than 0.01 wt.-%. According to a further embodiment, the micronized UV filter is either a UVA filter or a UVB filter or a broadband (UVA and UVB) filter.

According to a preferred embodiment, the micronized UV filter is a micronized insoluble, organic UV filter.

According to a preferred embodiment, the micronized UV filter according to the present invention is an insoluble, organic UV-filter having a mean particle size distribution $D_v50$ as determined by light scattering of less than 200 nm.

More preferably the micronized insoluble, organic UV filter has a mean particle size distribution $D_v50$ determined by light scattering (i.e. by Photon Correlation Spectroscopy (PCS)) selected in the range of 30 to 150 nm, most preferably in the range of 35 to 125 nm, such as in particular in the range of 40 to 110 nm. In a particular advantageous embodiment, the micronized insoluble organic UV absorber exhibits a $D_v10$ in the range of 50 to 80 nm, a $D_v50$ in the range of 75 to 125 nm and a $D_v90$ in the range of 140 to 180 nm, and even more preferably a $D_v10$ in the range of 55 to 75 nm, a $D_v50$ in the range of 80 to 110 nm and a $D_v90$ in the range of 150 to 175 nm. The particle size as given herein is generally determined in a suspension of the micronized insoluble organic UV absorber in water such as ultrapure water (Mili-Q purified), preferably at a concentration level of 3 mg/ml using a Beckman Coulter Delsa Nano S.

According to a further embodiment, the topical composition comprises the micronized UV filter as an aqueous dispersion containing micronized particles of micronized UV filter. Preferably, the concentration of the micronized UV filter in the aqueous dispersion is in the range of 10 to 90 wt-%, 20 to 80 wt-%, 30 to 70 wt-%, more preferably in the range of 40 to 60 wt-%, for instance in the range of 45 to 55 wt-%.

According to a further embodiment, the aqueous dispersion containing the micronized UV filter additionally contains a $C_{8-16}$alkyl poly-glucoside.

The term 'alkyl poly-glucoside (APG)' refers to a class of non-ionic surfactants having the generic formula $C_nH_{2+n}O(C_6H_{10}O_5)_xH$, in which n is an integer selected in the range of 2 to 22 and x refers to the mean polymerization level of the glucoside moiety (mono-, di-, tri-, oligo-, and poly-glucosides). These APG's are widely used in household and industrial applications. They are generally derived from renewable raw materials such as glucose derived from corn and plant derived fatty alcohols. These alkyl poly-glucosides generally exhibit a mean polymerisation level of the glucoside moiety ranging from 1 to 1.7, preferably from 1.2 to 1.6 such as from 1.4 to 1.6.

Particularly advantageous in all embodiments according to the present invention is the use of $C_{8-10}$ alkyl poly-glucoside consisting essentially of caprylyl ($C_8$) and capryl ($C_{10}$) poly-glucosides. Preferably such caprylyl ($C_8$) and capryl ($C_{10}$) poly-glucosides furthermore exhibit a ratio (%/%, wherein all % are area-% determined by HPLC-MS) of caprylyl ($C_8$) mono-glucoside to capryl ($C_{10}$) mono-glucoside in the range of 3:1 to 1:3, preferably in the range of about 2:1 to 1:2, most preferably in the range of 1.5:1 to 1:1.5. Additionally, such $C_{8-10}$ alkyl poly-glucoside preferably contain no more than 3 wt.-%, more preferably no more than 2 wt.-%, most preferably no more than 1.5 wt.-% of $C_{12}$ alkyl mono-glucoside (as determined by HPLC-MS). It is understood, that such alkyl poly-glucosides are basically free of any higher (i.e. $C1_{4-16}$) alkyl polyglucosides.

A particularly advantageous $C_{8-10}$ alkyl poly-glucoside according to the present invention is made from glucose derived from corn and $C_8$ and $C_{10}$ fatty alcohols derived from coconut and palm kernel oils, which is e.g. sold as an aqueous dispersion under the tradename Green APG 0810 by Shanghai Fine Chemical.

Preferably, such $C_{8-16}$alkyl poly-glucoside or mixtures thereof is/are present in a concentration of 2 to 15 wt.-%, preferably 5 to 10 wt.-%, based on the total weight of the aqueous dispersion. Preferably, such $C_{8-16}$alkyl poly-glucoside is $C_{8-10}$alkyl poly-glucoside.

According to a further embodiment, the micronized UV filter is methylene bis-benzotriazolyl tetramethylbutylphenol or tris-biphenyl triazine. In a preferred embodiment, the UV filter is micronized methylene bis-benzotriazolyl tetramethylbutylphenol.

Methylene bis-benzotriazolyl tetramethylbutylphenol (INCI), also referred to as MBBT, 2,2'-methylene-bis-(6-(2H-benzotriazole-2-yl)-4-(1,1,3,3-tetramethylbutyl)-phenol, is sold as an aqueous dispersion comprising MBBT and an alkyl poly-glucoside by DSM Nutritional Products Ltd (PARSOL® MAX) as well as by BASF SE (Tinosorb® M). Methylene bis-benzotriazolyl tetramethylbutylphenol is a broad-spectrum UV filter which filters UVA and UVB light.

Tris-biphenyl triazine is also referred to as 2,4,6-tris([1,1'-biphenyl]-4-yl)-1,3,5-Triazine, is a UV filter sold as Tinosorb® A2B by BASF SE.

In all embodiments of the present invention, the amount of the micronized UV filter (based on active), preferably of methylene bis-benzotriazolyl tetramethylbutylphenol or tris-biphenyl triazine, most preferably of methylene bis-benzotriazolyl tetramethylbutylphenol present in the topical compositions according to the present invention is advantageously selected in the range of 0.1 to 20 wt.-%, in particular in the range of 0.2 to 15 wt.-%, most particular in the range of 0.3 to 10 wt.-% based on the total weight of the composition. Further preferred ranges are 0.5 to 10 wt-%, 1 to 8 wt-% and 1 to 5 wt-% and 2 to 5 wt.-% based on the total weight of the composition.

In all embodiments of the present invention, the amount of panthenol present in the topical compositions according to the present invention is advantageously selected in the range of 0.001 to 10 wt.-%, preferably in the range of 0.01 to 7 wt-%, more preferably in the range of 0.1 to 6 wt-% and most preferably in the range of 0.5 to 5 wt-% based on the total weight of the composition. Further preferred ranges are 0.5 to 4.5 wt-%, 0.6 to 4 wt-%, 0.6 to 3.5 wt-%, 1 to 5 wt.-%, 2 to 5 wt.-%, 3 to 5 wt.-%, 1 to 6 wt.-%, 2 to 6 wt.-%, 3 to 6 wt.-% as well as 4 to 6 wt.-% of panthenol based on the total weight of the composition.

In all embodiments of the present invention, the amount of the hydroxyacetophenone present in the topical compositions according to the present invention is advantageously selected in the range of 0.001 to 5 wt.-%, preferably in the range of 0.01 to 4 wt-%, more preferably in the range of 0.1 to 3 wt-% based on the total weight of the composition. Further preferred ranges are 0.005 to 4.5 wt-%, 0.05 to 4.3 wt-%, and 0.25 to 2.9 wt-% as well as 0.25 to 2 wt.-% or 0.25 to 1 wt.-% based on the total weight of the composition.

One embodiment of the present invention relates to a method for the use of the micronized UV filter, in particular in combination with panthenol and a hydroxyacetophenone as described and defined herein in a topical composition according to the present invention for reducing the transfer of the topical composition to glass or plastic surfaces.

In a particular embodiment of the present invention relates to a method for the use of methylene bis-benzotriazolyl tetramethylbutylphenol, panthenol and p-hydroxyacetophenone in a topical composition according to the present invention for reducing the transfer of the topical composition to glass or plastic surfaces.

In another embodiment, the invention relates to the use of a micronized UV-filter, panthenol and a hydroxyacetophenone as described and defined to reduce the transfer of fat(s) and oil(s) contained in a topical composition according to the present invention to a surface such as in particular to a glass or plastic surface such as e.g. a touch screen.

In a further embodiment, the invention relates to a method to reduce the transfer of fat(s) and/or oil(s) to a surface such as in particular to a glass or plastic surface such as e.g. a touch screen, said method encompassing the addition of a micronized UV-filter, panthenol and hydroxyacetophenone as described and defined into a topical composition according to the present invention comprising such fat(s) and oil(s).

Preferred topical compositions in all embodiments of the present invention are emulsions containing an oily phase and an aqueous phase such as in particular an O/W, W/O, Si/W, W/Si, O/W/O, W/O/W multiple or a pickering emulsions. The amount of the oily phase (i.e. the phase containing all oils and fats) present in such emulsions is preferably at least 10 wt.-%, such as in the range of 10 to 60 wt.-%, preferably in the range of 15 to 50 wt.-%, most preferably in the range of 15 to 40 wt.-%, based on the total weight of the composition.

In a further embodiment, the present invention relates to the topical composition according to the embodiments described herein for the use as sunscreen, respectively to the use of the topical composition according to the embodiments described herein as sunscreen.

Besides the micronized UV filter, in particular micronized methylene bis-benzotriazolyl tetramethylbutylphenol or tris-biphenyl triazine, also further UV filters may be present in the topical composition according to the present invention. These UV filters are all commercially available UV-filter substances such as in particular (INCI names) polysilicone-15, phenylbenzimidazol sulfonic acid, 3-benzylidene camphor, octocrylene, ethylhexyl methoxycinnamate, ethylhexyl salicylate, homosalate, ethylhexyl triazone, zinc oxide, bis-ethylhexyloxyphenol methoxyphenyl triazine, diethylhexyl butamido triazone, benzophenon-3, titanium dioxide, butyl methoxydibenzoyl methane, disodium phenyl dibenzimidazole tetrasulfonate and diethylamino hydroxybenzoyl hexyl benzoate without being limited thereto. Preferably, the topical compositions according to the present invention comprise as further UV-filters at least octocrylene, ethylhexyl salicylate and butyl methoxydibenzoyl methane.

In another advantageous embodiment, the topical compositions according to the present invention are free of methylidene camphor (3-(4-methylbenzylidene)camphor) and/or octocrylene.

It is furthermore advantageous if the topical compositions according to the present invention are free of polyethylene glycol, polyethylene glycol ethers and polyethylene glycol esters (PEG-derivatives).

It is also advantageous if the topical compositions according to the present invention are free of parabens, benzethonium chloride, piroctone olamine, lauroyl arginate, benzoic acid, sorbic acid, methylisothiazolinone, chloromethylisothiazolinone, bronopol, benzalkonium chlorides, formaldehyde releasers, salicylic acid, triclosan, dehydroacetic acid, DMDM hydantoin, chlorphenesin, IPBC.

As the topical compositions according to the invention are intended for topical application, they comprise a physiologically acceptable medium, that is to say a medium compatible with keratinous substances, such as the skin, mucous membranes, and keratinous fibers. In particular the physiologically acceptable medium is a cosmetically acceptable carrier.

The term cosmetically acceptable carrier refers to all carriers and/or excipients and/or diluents conventionally used in cosmetic compositions.

Preferred topical compositions according to the invention are skin care preparations, decorative preparations, and functional preparations.

Examples of skin care preparations are, in particular, light protective preparations, anti-ageing preparations, preparations for the treatment of photo-ageing, body oils, body lotions, body gels, treatment creams, skin protection ointments, skin powders, moisturizing gels, moisturizing sprays, face and/or body moisturizers, skin-tanning preparations (i.e. compositions for the artificial/sunless tanning and/or browning of human skin), for example self-tanning creams as well as skin lightening preparations.

Examples of decorative preparations are, in particular, lipsticks, eye shadows, mascaras, dry and moist make-up formulations, rouges and/or powders.

Examples of functional preparations are cosmetic or pharmaceutical compositions containing active ingredients such as hormone preparations, vitamin preparations, vegetable extract preparations, anti-ageing preparations, and/or anti-microbial (antibacterial or antifungal) preparations without being limited thereto.

In a particular embodiment, the topical compositions according to the invention are light-protective preparations (sun care products), such as sun protection milks, sun protection lotions, sun protection creams, sun protection oils, sun blocks or day care creams with a SPF (sun protection factor). Of particular interest are sun protection creams, sun protection lotions, sun protection milks and sun protection preparations.

The topical compositions according to the present invention may be in the form of a suspension or dispersion in solvents or fatty substances, or alternatively in the form of an emulsion or micro emulsion (in particular of oil-in-water (O/W-) or water-in-oil (W/O-)type, silicone-in-water (Si/W-) or water-in-silicone (W/Si-)type, PIT-emulsion, multiple emulsion (e.g. oil-in-water-in oil (O/W/O-) or water-in-oil-in-water (W/O/W-)type), pickering emulsion, hydrogel, alcoholic gel, lipogel, one- or multiphase solution or vesicular dispersion or other usual forms, which can also be applied by pens, as masks or as sprays.

The topical compositions according to the present invention are advantageously in the form of an oil-in-water (O/W) emulsion comprising an oily phase dispersed in an aqueous phase in the presence of an O/W emulsifier. The preparation of such O/W emulsions is well known to a person skilled in the art and illustrated in the examples.

In one advantageous embodiment, the O/W emulsifier according to the present invention is a phosphate ester emulsifier. The term phosphate ester emulsifier refers to phosphate esters emulsifier of formula (II)

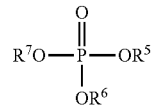

formula (II)

wherein $R^5$, $R^6$ and $R^7$ may be hydrogen, an alkyl of from 1 to 22 carbons, preferably from 12 to 18 carbons; or an alkoxylated alkyl having 1 to 22 carbons, preferably from 12 to 18 carbons, and having 1 or more, preferably from 2 to 25, most preferably 2 to 12, moles ethylene oxide, with the provision that at least one of $R^5$, $R^6$ and $R^7$ is an alkyl or alkoxylated alkyl as previously defined but having at least 6 alkyl carbons in said alkyl or alkoxylated alkyl group.

Monoesters in which $R^5$ and $R^6$ are hydrogen and $R^7$ is selected from alkyl groups of 10 to 18 carbons and alkoxylated fatty alcohols of 10 to 18 carbons and 2 to 12 moles ethylene oxide are preferred. Among the preferred phosphate ester emulsifier are $C_8$-1 Alkyl Ethyl Phosphate, $C_{9-15}$ Alkyl Phosphate, Ceteareth-2 Phosphate, Ceteareth-5 Phosphate, Ceteth-8 Phosphate, Ceteth-10 Phosphate, Cetyl Phosphate, $C_{6-10}$ Pareth-4 Phosphate, $C_{12-15}$ Pareth-2 Phosphate, $C_{12-15}$ Pareth-3 Phosphate, DEA-Ceteareth-2 Phosphate, DEA-Cetyl Phosphate, DEA-Oleth-3 Phosphate, Potassium cetyl phosphate, Deceth-4 Phosphate, Deceth-6 Phosphate and Trilaureth-4 Phosphate. A particular phosphate ester emulsifier according to the invention is potassium cetyl phosphate e.g. commercially available as Amphisol® K at DSM Nutritional Products Ltd Kaiseraugst.

Further suitable O/W emulsifiers according to the present invention encompass PEG-30 Dipolyhydroxystearate, PEG-4 Dilaurate, PEG-8 Dioleate, PEG-40 Sorbitan Peroleate, PEG-7 Glyceryl Cocoate, PEG-20 Almond Glycerides, PEG-25 Hydrogenated Castor Oil, Glyceryl Stearate (and) PEG-100 Stearate, PEG-7 Olivate, PEG-8 Oleate, PEG-8 Laurate, PEG-60 Almond Glycerides, PEG-20 Methyl Glucose Sesquistearate, PEG-40 Stearate, PEG-100 Stearate, PEG-80 Sorbitan Laurate, Steareth-2, Steareth-12, Oleth-2, Ceteth-2, Laureth-4, Oleth-10, Oleth-10/Polyoxyl 10 Oleyl Ether, Ceteth-10, Isosteareth-20, Ceteareth-20, Oleth-20, Steareth-20, Steareth-21, Ceteth-20, Isoceteth-20, Laureth-23, Steareth-100, glycerylstearatcitrate, glycerylstearate (self-emulsifying), stearic acid, salts of stearic acid, polyglyceryl-3-methylglycosedistearate. Further suitable emulsifiers are sorbitan oleate, sorbitan sesquioleate, sorbitan isostearate, sorbitan trioleate, Lauryl Glucoside, Decyl Glucoside, Sodium Stearoyl Glutamate, Sucrose Polystearate and Hydrated Polyisobuten. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof.

Another particular suitable class of O/W emulsifiers are non-ionic self-emulsifying system derived from olive oil e.g. known as (INCI Name) cetearyl olivate and sorbitan olivate (Chemical Composition: sorbitan ester and cetearyl ester of olive oil fatty acids) sold under the tradename OLIVEM 1000.

Further suitable are commercially available polymeric emulsifiers such as hydrophobically modified polyacrylic acid such as Acrylates/C10-30 Alkyl Acrylate Crosspolymers which are commercially available under the tradename Pemulen® TR-1 and TR-2 by Noveon. Another class of particularly suitable emulsifiers are polyglycerol esters or diesters of fatty acids also called polyglyceryl ester/diester (i.e. a polymer in which fatty acid(s) is/are bound by esterification with polyglycerine), such as e.g. commercially available at Evonik as Isolan GPS [INCI Name Polyglyceryl-4 Diisostearate/Polyhydroxystearate/Sebacate (i.e. diester of a mixture of isostearic, polyhydroxystearic and sebacic acids with Polyglycerin-4)] or Dehymuls PGPH available at Cognis (INCI Polyglyceryl-2 Dipolyhydroxystearate).

Also suitable are polyalkylenglycolether such as Brij 72 (Polyoxyethylen(2)stearylether) or Brij 721 (Polyoxyethylene (21) Stearyl Ether e.g. available at Croda.

The at least one O/W respectively Si/W emulsifier is preferably used in an amount of 0.5 to 10 wt.-% such as in particular in the range of 0.5 to 5 wt.-% such as most in particular in the range of 0.5 to 4 wt.-% based on the total weight of the composition.

Suitable W/O- or W/Si-emulsifiers are polyglyceryl-2-dipolyhydroxystearat, PEG-30 dipolyhydroxystearat, cetyl dimethicone copolyol, polyglyceryl-3 diisostearate polyglycerol esters of oleic/isostearic acid, polyglyceryl-6 hexaricinolate, polyglyceryl-4-oleate, polygylceryl-4 oleate/PEG-8 propylene glycol cocoate, magnesium stearate, sodium stearate, potassium laurate, potassium ricinoleate, sodium cocoate, sodium tallowate, potassium castorate, sodium oleate, and mixtures thereof. Further suitable W/Si-emulsifiers are Lauryl Polyglyceryl-3 Polydimethylsiloxyethyl Dimethicone and/or PEG-9 Polydimethylsiloxyethyl Dimethicone and/or Cetyl PEG/PPG-10/1 Dimethicone and/or PEG-12 Dimethicone Crosspolymer and/or PEG/PPG-18/18 Dimethicone. The at least one W/O emulsifier is preferably used in an amount of about 0.001 to 10 wt.-%, more preferably in an amount of 0.2 to 7 wt.-% with respect to the total weigh of the composition.

The topical compositions according to the present invention furthermore advantageously contain at least one co-surfactant such as e.g. selected from the group of mono- and diglycerides and/or fatty alcohols. The co-surfactant is generally used in an amount selected in the range of 0.1 to 10 wt.-%, such as in particular in the range of 0.5 to 7 wt.-%, such as most in particular in the range of 1 to 5 wt.-%, based on the total weight of the composition. Particular suitable co-surfactants are selected from the list of alkyl alcohols such as cetyl alcohol (Lorol C16, Lanette 16), cetearyl alcohol (Lanette O), stearyl alcohol (Lanette 18), behenyl alcohol (Lanette 22), glyceryl stearate, glyceryl myristate (Estol 3650), hydrogenated coco-glycerides (Lipocire Na10) as well as mixtures thereof.

The compositions in form of O/W emulsions according to the invention can be provided, for example, in all the formulation forms for O/W emulsions, for example in the form of serum, milk or cream, and they are prepared according to the usual methods. The compositions which are subject-matters of the invention are intended for topical application and can in particular constitute a dermatological or cosmetic composition, for example intended for protecting human skin against the adverse effects of UV radiation (antiwrinkle, anti-ageing, moisturizing, anti-sun protection and the like).

According to an advantageous embodiment of the invention the compositions constitute cosmetic composition and are intended for topical application to the skin.

Finally, a subject-matter of the invention is a method for the cosmetic treatment of keratinous substances such as in particular the skin, wherein a composition as defined above is applied to the said keratinous substances such as in particular to the skin. The method is in particular suitable to protect the skin against the adverse effects of UV-radiation such as in particular sun-burn and/or photoageing.

In accordance with the present invention, the compositions according to the invention may comprise further ingredients such as ingredients for skin lightening; tanning prevention; treatment of hyperpigmentation; preventing or reducing acne, wrinkles, lines, atrophy and/or inflammation; chelators and/or sequestrants; anti-cellulites and slimming (e.g. phytanic acid), firming, moisturizing and energizing, self-tanning, soothing, as well as agents to improve elasticity and skin barrier and/or further UV-filter substances and carriers and/or excipients or diluents conventionally used in topical compositions. If nothing else is stated, the excipients, additives, diluents, etc. mentioned in the following are suitable for topical compositions according to the present invention. The necessary amounts of the cosmetic and dermatological adjuvants and additives can, based on the desired product, easily be determined by the skilled person. The additional ingredients can either be added to the oily phase, the aqueous phase or separately as deemed appropriate. The mode of addition can easily be adapted by a person skilled in the art.

The cosmetically active ingredients useful herein can in some instances provide more than one benefit or operate via more than one mode of action.

The topical cosmetic compositions of the invention can also contain usual cosmetic adjuvants and additives, such as preservatives/antioxidants, fatty substances/oils, water, organic solvents, silicones, thickeners, softeners, emulsifiers, sunscreens, antifoaming agents, moisturizers, aesthetic components such as fragrances, surfactants, fillers, sequestering agents, anionic, cationic, nonionic or amphoteric polymers or mixtures thereof, propellants, acidifying or basifying agents, dyes, colorings/colorants, abrasives, absorbents, essential oils, skin sensates, astringents, antifoaming agents, pigments or nanopigments, e.g. those suited for providing a photoprotective effect by physically blocking out ultraviolet radiation, or any other ingredients usually formulated into cosmetic compositions. Such cosmetic ingredients commonly used in the skin care industry, which are suitable for use in the compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the cosmetic and dermatological adjuvants and additives can—based on the desired product—easily be chosen by a skilled person in this field and will be illustrated in the examples, without being limited hereto.

Of course, one skilled in this art will take care to select the above mentioned optional additional compound or compounds and/or their amounts such that the advantageous properties intrinsically associated with the combination in accordance with the invention are not, or not substantially, detrimentally affected by the envisaged addition or additions.

The topical compositions according to the invention in general have a pH in the range of 3 to 10, preferably a pH in the range of 4 to 8 and most preferably a pH in the range of 4 to 7.

The pH can easily be adjusted as desired with suitable acids such as e.g. citric acid or bases such as NaOH according to standard methods in the art.

The topical compositions according to the invention may further contain one or more emollients which soothe and soften the skin. As an example, the emollient may be dicaprylyl carbonate or $C_{12-15}$alkyl benzoate. Further emollients are silicone (dimethicone, cyclomethicone), vegetable oils (grape seed, sesame seed, jojoba, etc.), butters (cocoa butter, shea butter), alcohols (stearyl alcohol, cetyl alcohol), and petrolatum derivatives (petroleum jelly, mineral oil).

The cosmetic compositions according to the present invention advantageously comprise preservatives or preservative booster. Preferably, the additional preservatives respectively preservative booster is selected from the group consisting of phenoxyethanol, ethylhexylglycerin, glyceryl caprylate, caprylyl glycol, 1,2-hexanediol, propanediol, propylene glycol as well as mixtures thereof. When present, the preservative respectively preservative booster is preferably used in an amount of 0.01 to 2 wt.-%, more preferably in an amount of 0.05 to 1.5 wt.-%, most preferably in an amount of 0.1 to 1.0 wt.-%, based on the total weight of the composition. It is particularly preferred, that the cosmetic compositions according to the invention does not contain any further/other preservatives such as e.g. parabens and/or methylisothiazolidine.

Put a microscope slide (glass plate) on top of the sponge with 500 g pressure for 10 seconds Weigh the amount of cream transferred to the glass plate (transfer in [mg])

Repeat the test for each formulation 10 times to receive an average value for each formulation The results are outlined in table 2.

TABLE 1

| O/W emulsion | |
|---|---|
| INCI | Wt.-% |
| Butyl Methoxydibenzoyl Methane | 4.00 |
| Octocrylene | 8.00 |
| Ethylhexyl Salicylate | 5.00 |
| Potassium Cetyl Phosphate | 1.50 |
| Cetyl alcohol | 3.00 |
| Dicaprylyl Carbonate | 8.00 |
| C12-15 Alkyl Benzoate | 8.00 |
| Aqua | Ad 100 |
| Glycerin | 3.00 |
| Xanthan Gum | 0.30 |
| Hydroxyacetophenone (HAP) | See table 2 |
| Panthenol | See table 2 |
| Methylene Bis-Benzotriazolyl Tetrannethylbutylphenol (50% active), Aqua, Decyl Glucoside, Propylene Glycol, Xanthan Gum (MBBT) | See table 2 |
| Phenoxyethanol, Ethylhexylglycerin | 1.00 |

TABLE 2

| transfer of cream in dependence of ingredients | | | | | | | | | |
|---|---|---|---|---|---|---|---|---|---|
| | INCI | | | | | | | | |
| | Placebo | Ref-1 | Ref-2 | Ref-3 | Ref-4 | Ref-5 | Ref-6 | Inv-1 | Inv-2 | Inv-3 |
| | | | | | Wt.-% | | | | | |
| HAP | — | 0.5 | — | — | — | 0.5 | 0.5 | 0.5 | 0.5 | 0.5 |
| Panthenol | — | — | 1.0 | 3.0 | — | 1.0 | 3.0 | 1.0 | 3.0 | 5.0 |
| MBBT | — | — | — | — | 8.0 | — | — | 8.0 | 8.0 | 8.0 |
| Transfer [%] | 3.8 | 3.7 | 2.0 | 4.0 | 4.0 | 3.7 | 3.3 | 1.1 | 1.5 | 0.8 |

The following examples are provided to further illustrate the compositions and effects of the present invention. These examples are illustrative only and are not intended to limit the scope of the invention in any way.

Experimental Part

The formulations (O/W emulsions) as outlined in table 1 have been prepared according to standard methods in the art.

Then the transfer resistance has been tested with the sponge test as outlined below (Test always performed in the same test set-up (same day, person, temperature, humidity etc. etc.):
Cut a sponge cloth into pieces of 7.5 cm×2.5 cm
Tare the sponge sample
Apply 400 mg cream and distribute homogenously all over the sponge surface of 7.5×2.5 cm
Weigh the sponge with the applied sample
Tare microscope slide (glass plate)

As can be retrieved from table 2, only the addition of p-HAP, panthenol and MBBT to the topical composition significantly reduced the amount of cream transferred to the glass surface.

The invention claimed is:
1. A topical composition consisting of:
   1 to 5 wt. %, based on total weight of the composition, of panthenol,
   0.5 to 5 wt. %, based on total weight of the composition, of p-hydroxyacetophenone,
   0.3 to 10 wt. %, based on total weight of the composition, of methylene bis-benzotriazolyl tetramethylbutylphenol (MBBT) as a micronized UV filter, and
   optionally at least one additional UV filter selected from the group consisting of butyl methoxydibenzoylmethane, octocrylene and ethylhexyl salicylate,
   wherein the micronized UV filter is present as an aqueous dispersion containing the particles of the micronized UV filter optionally with a $C_{8-16}$ alkyl poly-glucoside, wherein the micronized UV filter has a mean particle size distribution Dv50 as determined by light scattering of less than 200 nm, wherein the composition is an oil-in-water (O/W) emulsion consisting of an oily phase dispersed in an aqueous phase, wherein the aqueous phase consists of the micronized UV filter in the presence of a phosphate ester emulsifier as an O/W emulsifier, and wherein the topical composition exhibits less transfer of the composition to a glass surface as compared to an identical composition that does not contain the panthenol, the p-hydroxyacetophenone and the MBBT.

2. The topical composition according to claim 1, wherein the micronized UV filter is present in an amount of 1 to 8 wt. %, based on the total weight of the composition.

3. The topical composition according to claim 1, wherein the panthenol is present in an amount of 3 to 5 wt. %, based on the total weight of the composition.

4. The topical composition according to claim 1, wherein the p-hydroxyacetophenone is present in an amount of 0.5 to 1 wt. %, based on the total weight of the composition.

5. The topical composition according to claim 1, wherein the O/W emulsifier is potassium cetyl phosphate.

6. The topical composition according to claim 1, wherein the topical composition further consists of at least one additional UV filter selected from the group consisting of butyl methoxydibenzoylmethane, octocrylene and ethylhexyl salicylate.

\* \* \* \* \*